United States Patent
Duan et al.

(10) Patent No.: US 9,192,162 B2
(45) Date of Patent: Nov. 24, 2015

(54) USE OF POLYHEXAMETHYLENE GUANIDINE HYDROCHLORIDE AS PRESERVATIVE TO CONTROL CITRUS SOUR ROT AND ITS APPLICATION

(75) Inventors: Xuewu Duan, Guangdong (CN); Yueming Jiang, Guangdong (CN); Linyan Feng, Guangdong (CN); Fuwang Wu, Guangdong (CN)

(73) Assignee: SOUTH CHINA BOTANICAL GARDEN, CHINESE ACADEMY OF SCIENCES, Tianhe, Guangzhou, Guangdong (CN)

( * ) Notice: Subject to any disclaimer, the term of this patent is extended or adjusted under 35 U.S.C. 154(b) by 14 days.

(21) Appl. No.: 13/885,165

(22) PCT Filed: Nov. 15, 2010

(86) PCT No.: PCT/CN2010/078754
§ 371 (c)(1),
(2), (4) Date: May 14, 2013

(87) PCT Pub. No.: WO2012/062001
PCT Pub. Date: May 18, 2012

(65) Prior Publication Data
US 2013/0245079 A1   Sep. 19, 2013

(30) Foreign Application Priority Data
Nov. 14, 2010  (CN) .......................... 2010 1 0542278

(51) Int. Cl.
| | | |
|---|---|---|
| *A01N 47/44* | (2006.01) | |
| *A01N 43/50* | (2006.01) | |
| *A23B 7/154* | (2006.01) | |
| *C08L 79/04* | (2006.01) | |
| *A01N 43/78* | (2006.01) | |
| *A01N 47/18* | (2006.01) | |
| *A01N 47/34* | (2006.01) | |
| *A23L 3/3463* | (2006.01) | |
| *C08L 71/02* | (2006.01) | |

(52) U.S. Cl.
CPC ................ *A01N 47/44* (2013.01); *A01N 43/50* (2013.01); *A01N 43/78* (2013.01); *A01N 47/18* (2013.01); *A01N 47/34* (2013.01); *A23B 7/154* (2013.01); *A23L 3/3463* (2013.01); *C08L 71/02* (2013.01); *C08L 79/04* (2013.01)

(58) Field of Classification Search
CPC ............................... A01N 47/44; A01N 43/50
USPC .................. 424/405; 504/139, 275, 343, 345
See application file for complete search history.

(56) References Cited

U.S. PATENT DOCUMENTS

2006/0276468 A1* 12/2006 Blow .......................... 514/232.5
2009/0275663 A1* 11/2009 Balekhov et al. ............. 514/634

FOREIGN PATENT DOCUMENTS

| CN | 1390876 A | 1/2003 |
|---|---|---|
| CN | 101263837 A | 9/2008 |
| CN | 101263837 B | 6/2010 |

OTHER PUBLICATIONS

Wei et al. Materials Science and Engineering C 2009, 29, 1776-1780.*
Brown et al., "Evaluation of polyhexamethylene biguanide for control of postharvest diseases of florida citrus," Proc. Fla. State Hort. Soc. 1999, No. 112, pp. 118-121.
Zhan et al., "Research advances in organic guanidine antimicrobial," International Textile Guiding Report, No. 5, 2009, pp. 47-48.50-52. 54.
Liu et al., "Efficacy of biological control sour rot of citrus fruit by *Cryptococcus laurentii*," Journal of Zhejiang Normal University (National Science version), vol. 33, No. 1, Mar. 2010, pp. 14-17.
"International Search Report" mailed on Aug. 25, 2011 for International application No. PCT/CN2010/078754, International filed:Nov. 15, 2010.

* cited by examiner

*Primary Examiner* — Sreeni Padmanabhan
*Assistant Examiner* — Irina Neagu
(74) *Attorney, Agent, or Firm* — Winston Hsu; Scott Margo

(57) ABSTRACT

The use of polyhexamethylene guanidine hydrochloride as preservative for preventing and controlling citrus sour rot and its application are disclosed by the present invention. The citrus preservative calculated by 100% total mass fraction comprises 0.05%-0.5% polyhexamethylene guanidine hydrochloride, 0.05%-0.2% of one or more selected from the group consisting of a mixture of several of the following: 0.05%-0.2% imidazole fungicidebactericide, benzimidazole fungicidebactericide, pyrimethanil, fludioxonil and azoxystrobin, and 0.02%-0.15% polyethenoxy ether emulsion or quaternary ammonium salt emulsion, and the rest is water. The citrus preservative can significantly inhibit the decay of citrus fruit such as Citrus microcarpa during storage, especially the incidence of sour rot. So the commercial value of citrus is obviously increased.

7 Claims, 3 Drawing Sheets

USE OF POLYHEXAMETHYLENE GUANIDINE HYDROCHLORIDE AS PRESERVATIVE TO CONTROL CITRUS SOUR ROT AND ITS APPLICATION

CROSS REFERENCE TO RELATED APPLICATION

This application is a national stage application under 35 U.S.C. §371 of PCT/CN2010/078754, filed Nov. 15, 2010, which claims benefit to Chinese application No. 201010542278.3, filed Nov. 14, 2010, the entire disclosures of all of which are hereby incorporated by reference.

BACKGROUND OF THE INVENTION

1. Field of the Invention

The invention belongs to the field of storage of fruits and specifically relates to an application of polyhexamethylene guanidine hydrochloride in the control of citrus sour rot and a citrus preservative.

2. Description of the Prior Art

Citrus is the first major fruit around the world, and is cultivated in 138 countries with the area of about 6.67 million hectares and the annual total output of more than one hundred million tons, wherein the annual total output accounts for 22% of the total output of fruits around the world. According to statistics, in 2008, the citrus cultivation area in China achieved 30.45 million mus, the total output was 23.31 million tons and accounted for about 23% of the citrus output around the world, and China was the largest citrus production country in the world. Guangdong province is one of the main citrus producing areas in China, and 'Shatang' mandarin are the most unique variety in the citrus varieties in Guangdong province and are very competitive in fruit markets at home and abroad. However, due to the unique biological characteristics, 'Shatang' mandarin are difficult to store in comparison with other citrus fruits, the post-harvest loss is quite serious, and the annular loss is above hundreds of million Chinese yuan (CHY), so that the development of the industry of 'Shatang' mandarin is seriously restricted.

Citrus belongs to a non-climacteric fruit, but the vigorous post-harvest respiratory metabolism can cause the rapid decline in nutrition and flavor quality. 'Shatang' mandarin fruit are characterized by thin in skin, juicy and vulnerable to post-harvest diseases, which make it difficult to store. The main post-harvest diseases for the fruit include sour rot, green and blue mold, black rot and blossom-end rot. At present, the most effective way to control the decay of 'Shatang' mandarin fruit is the application of low-temperature in combination with chemical bactericides. The bactericides include carbendazim, mildothane, imazalil, guazatine, and the like, but the way is still not very ideal to control the decay, in particular to the sour rot.

At present, the sour rot is one of the diseases which are most common and most difficult to control during storage and transportation of 'Shatang' mandarin fruit. The pathogenic fungi are *Geotrichum candidum* in Hyphomycetes, Deuteromycota, which infect the fruit through the damaged part. *Geotrichum candidum* only infects the fruit, generally mature or overripe fruits, and in particular to the fruit during the storage period. The incidence rate of sour rot is affected by preharvest cultivation measures, maturity, harvesting methods, fruit water status, storage and transportation measures and other factors. For example, the incidence rate of the sour rot in the main production area of 'Shatang' mandarin in Guangdong province in 2007 was below 10%, while the incidence rate at the beginning of 2010 was as high as above 50% due to the weather. Sour rot has not been controlled efficiently by imidazole and benzimidazole. Guazatine is effective to control sour rot in citrus fruit, but the use of guazatine was very limited due to pesticide residues and safety issue. Considering carcinogenic risk, Guazatine has been forbidden in USA Therefore, it is imperative to seek a safe, efficient and simple technology to control sour rot in citrus.

PHMG (polyhexamethylene guanidine hydrochloride, polyhexamethylene guanidine) is an environment-friendly broad-spectrum antibacterial agent newly synthesized internationally. PHMG belongs to guanidine derivatives and is a cationic polymer. PHMG can efficiently kill bacteria by attacking the cellular wall and cytoplasma membrane systems. PHMG can rapidly break through cytoplasma membranes when it combine with the fatty acids in phospholipid of cell membrane, breach nuclei of cells of the pathogenic bacteria, enable cell inclusion of the pathogenic bacteria to outflow. PHMG is a polymer and less prone to being absorbed by animal, so that its toxicity can be greatly reduced. According to the results of Russian quarantine departments, the half lethal dose (LD50) of PHMG to mice is 25,000 mg/kg, so that PHMG is at actually non-toxic level. As PHMG has the characteristics of no toxicity, high efficiency, stability and the like, PHMG can be widely applied to hospital sterilization and sterilization of drinking water and food processing equipments. PHMG has strong effects of killing and inhibiting bacteria and viruses, and the studies and the applications in the effect of inhibiting fungi are fewer. At present, there have been no reports about the application and studies of PHMG in the control of post-harvest fruit and vegetable fungal disease.

SUMMARY OF THE INVENTION

The first object of the invention is to provide an application of polyhexamethylene guanidine hydrochloride in controlling citrus sour rot.

In the invention, an antifungai material, namely polyhexamethylene guanidine hydrochloride, was chosen by experiments in vitro and in vivo, which can obviously inhibit the growth of *Geotrichum candidum* and effectively reduce the incidence of the sour rot in 'Shatang' mandarin fruit. A preservative obtained by combining polyhexamethylene guanidine hydrochloride with the bactericides for control the green and blue mold can effectively inhibit the decay, in particular to the sour rot, in loose-skin mandarin fruit during storage and circulation processes.

Therefore, the second object of the invention is to provide a preservative which is specially used to control the rot in post-harvest citrus, in particular to the sour rot.

Calculated based on 100% total mass fraction, the citrus preservative comprises 0.05%-0.5% of polyhexamethylene guanidine hydrochloride, 0.05%-0.2% of one or more selected from the group consisting of imidazole bactericide, benzimidazole bactericide, pyrimethanil, fludioxonil and azoxystrobin, 0.02%-0.15% of polyethenoxy ether or quaternary ammonium salt emulsifier and the balance water.

Preferably, the imidazole bactericide is prochloraz or imazalil.

Preferably, the benzimidazole bactericide is carbendazim, mildothane or tecto.

The mass fraction of polyhexamethylene guanidine hydrochloride is 0.1%-0.5% preferably, and 0.25%-0.5% more preferably.

The preparation method of the citrus preservative according to the present invention is as follows: firstly mixing an emulsifier with polyhexamethylene guanidine hydrochloride, further adding one or a mixture of several of an imidazole bactericide, a benzimidazole bactericide, pyrimethanil, fludioxonil and azoxystrobin as the preservative and a small amount of water and uniformly stirring to get a product; and when the citrus preservative is used, water is further added for diluting till the above concentration is reached so as to get the citrus preservative disclosed by the invention.

The citrus preservative disclosed by the invention can obviously inhibit the occurrence of the rot, in particular to the sour rot of 'Shatang' mandarin and other citrus fruits during the storage period. For example, after the 'Shatang' mandarin fruit are treated by the citrus preservative disclosed by the invention and then stored for 45 days at normal temperature (15-25° C.), the incidence of the sour rot is lower than 10%, while the incidence of the sour rot in the control group is as high as 60%, so that the citrus preservative disclosed in the invention can significantly reduce the occurrence of the sour rot of the loose-skin mandarin during storage and greatly improve the economic value of citrus.

DETAILED DESCRIPTION

The following embodiments are used for further describing the invention rather than limiting the invention.

In the following embodiments, carbendazim is 2-benzimidazolyl-methyl-carbamate, mildothane is 1,2-bis(3-methoxycarbonyl-2-thioureido)benzene, tecto is 2-(thiazol-4-yl) benzimidazole, prochloraz is N-propyl-N-[2-(2,4,6-trichlorophenoxy)ethyl]-imidazole-1-methanamide, and imazalil is 1-[2-(2,4-dichlorophenyl)-2-(2-allyloxy)]-1H-imidazole.

Antifungal Experiments In Vitro

1. Materials and Methods (1) Strain: *Geotrichum candidum* were isolated and purified from 'Shatang' mandarin fruit with sour rot.

(2) Spore germination test: A spore suspension method was adopted. A certain calculated amount of PHMG agent was respectively added into a ½ PBD culture medium which had been sterilized to prepare 9 concentration gradients: 0, 0.1, 1, 2, 5, 10, 20, 50 and 100 mg/L. The 5 ml culture media with the different concentrations of PHMG were respectively taken and put into 10 ml sterilized test tubes, 0.1 ml prepared standard spore suspension was further added into each test tube, shaking culture was performed at 250 rpm/min and a constant temperature of 26° C. for 8 hours, then 1-2 drops of bacterial liquid was taken out and observed under a microscope, the spore germination number was determined and the spore germination rate was further calculated.

(3) Mycelial growth test: Filter paper method of bacteriostatic circle was adopted. A prepared PDA culture medium which was sterilized by high-pressure steam was cooled to 45-50° C., the *Geotrichum candidum* spore suspension was added into the culture medium, the spore concentration is $10^6$/L, and the culture medium was poured into a sterilized culture disk to prepare a flat plate. A sterilized filter paper sheet with the diameter of 5 mm was placed at the center of the flat plate, 10 μl of 1 g/L PHMG solution (sterile water was used for replacing PHMG as control) was added on the filter paper, then culture was performed in a constant temperature incubator at 26° C. for 5 days, and the diameter of a filer paper inhibition zone was measured and analyzed.

(4) Scanning electron microscope observation of mycelium: the prepared PDA culture medium was sterilized by high-pressure steam, cooled to 45-50° C., added with the final concentration of 10 mg/L PHMG, and then poured into the sterilized culture dish to forma flat plate. *Geotrichum candidum* spore suspension was inoculated on the PDA culture medium and then cultured in the constant temperature incubator at 26° C. for 5 days. Mycelia were cut from the edge of a colony by a hole puncher with the diameter of 0.4 cm, and subjected to the scanning electron microscope observation according to the conventional method.

2. Experimental Results

Figure 1:
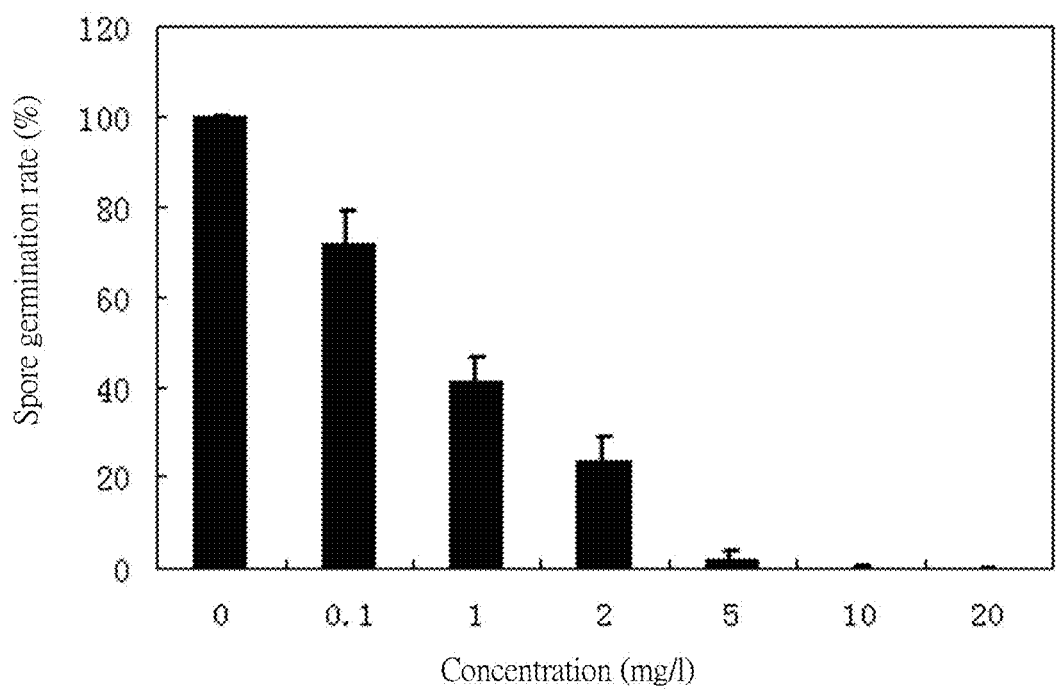
FIG. 1 is a diagram showing the influence of PHMG at different concentrations on spore germination of *Geotrichum candidum* in vitro.
Figure 2:
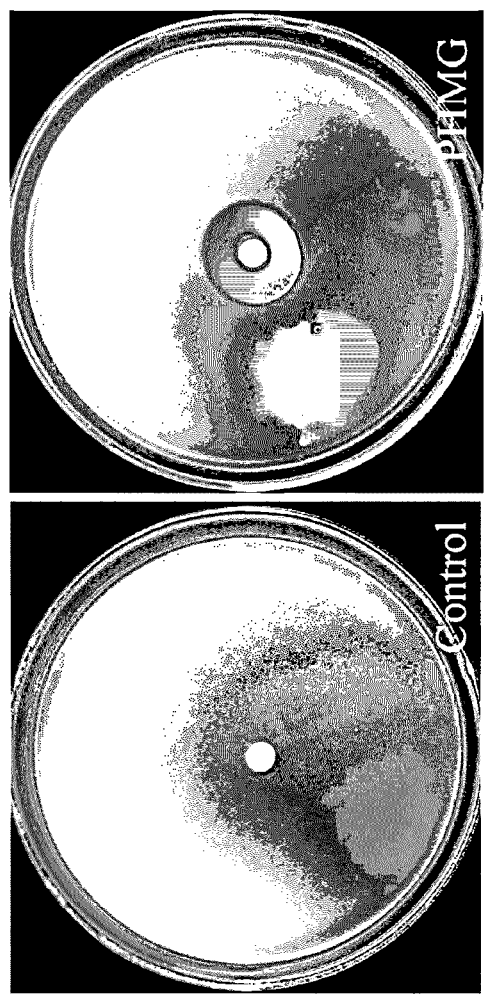
FIG. 2 is a diagram showing the inhibitory effect of PHMG on mycelial growth of *Geotrichum candidum* (by a filter paper inhibition zone method) in vitro.
Figure 3:
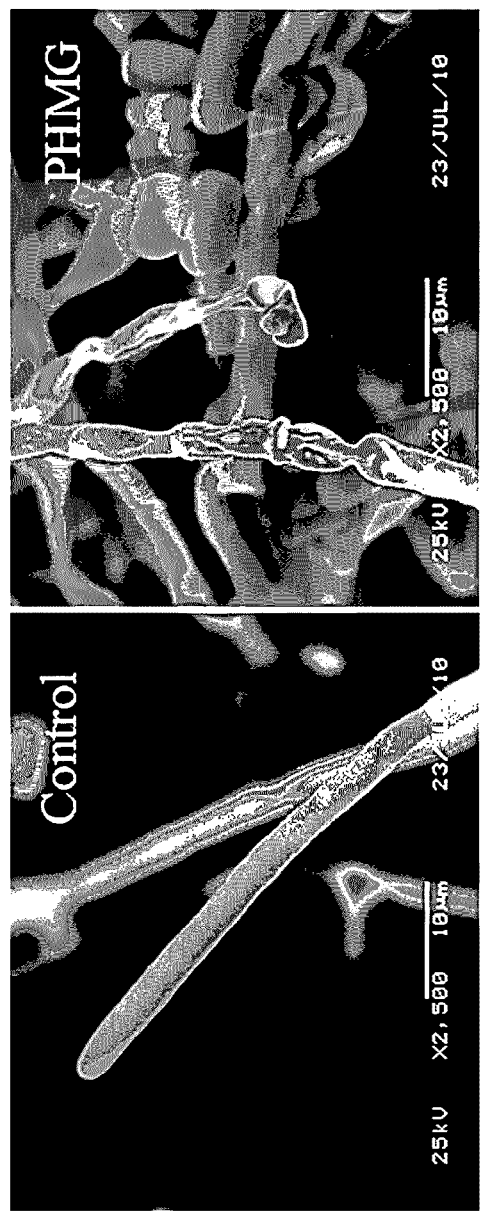
FIG. 3 is a scanning electron microscope image of mycelial growth of *Geotrichum candidum* on a culture medium containing PHMG.

As shown in FIG. 1, PHMG can significantly inhibit the spore germination of *Geotrichum candidum* in a concentration-dependent pattern in vitro. When the concentration of PHMG is 5 mg/L, the spore germination rate of *Geotrichum candidum* is only 2.13%, and 10 mg/L PHMG can almost completely inhibit the spore germination of *Geotrichum candidum* from 'Shatang' mandarin fruit. The experiment using Filter paper method of bacteriostatic circle shows that the filter paper sheet containing 10 μl of 1 g/L PHMG has the significant inhibitory effect on the mycelial growth of *Geotrichum candidum*, and the diameter of the inhibition zone is 2.19 cm after 5 days of culture at 26° C. (FIG. 2). From FIG. 3, it shows that, in the PDA culture medium free of PHMG, the mycelial growth of *Geotrichum candidum* is normal, the mycelia are rod-like, uniform and smooth in surfaces, but in the culture medium containing PHMG, the mycelia have severe distortion and surface depression, so that the inhibitory effect of PHMG on the mycelial growth is further proved.

In summary, polyhexamethylene guanidine hydrochloride (PHMG) can be applied to control sour rot in citrus fruits.

II. Citrus Preservative

Embodiment 1

5 g of PHMG was mixed with 2 g of polyquaternary salt-7, then 10 g of carbendazim and a small amount of water were added, uniform stirring is performed, water was finally added till the total weight achieved 10 kg, and uniform stirring was performed to get the citrus preservative of the embodiment; and the citrus preservative was used for soaking 'Shatang' mandarin fruit.

Embodiment 2

25 g of PHMG was mixed with 2 g of didecyl dimethyl ammonium chloride, then 10 g of mildothane and a small amount of water were added, uniform stirring was performed, water was finally added till the total weight achieved 10 kg, and uniform stirring was performed to get the citrus preservative of the embodiment; and the citrus preservative was used for soaking 'Shatang' mandarin fruit.

Embodiment 3

50 g of PHMG was mixed with 15 g of castor oil polyoxyethylene ether agricultural emulsifier BY120, then 20 g of tecto and a small amount of water were added, uniform stirring was performed, water was finally added till the total weight achieved 10 kg, and uniform stirring was performed to get the citrus preservative of the embodiment; and the citrus preservative was used for soaking 'Shatang' mandarin fruit.

Embodiment 4

10 g of PHMG was mixed with 4 g of dodecyl trimethyl ammonium chloride, then 10 g of prochloraz and a small amount of water were added, uniform stirring was performed, water was finally added till the total weight achieved 10 kg, and uniform stirring was performed to get the citrus preservative of the embodiment; and the citrus preservative was used for soaking 'Shatang' mandarin fruit.

Embodiment 5

10 g of PHMG was mixed with 5 g of polyoxyethylene nonyl phenyl ether agricultural emulsifier No. 100, then 10 g of imazalil and a small amount of water were added, uniform stirring was performed, water was finally added till the total weight achieved 10 kg, and uniform stirring was performed to get the citrus preservative of the embodiment; and the citrus preservative was used for soaking 'Shatang' mandarin fruit.

Embodiment 6

5 g of PHMG was mixed with 5 g of castor oil polyoxyethylene ether agricultural emulsifier BY120, then 5 g of tecto, 5 g of imazalil and a small amount of water were added, uniform stirring was performed, water was finally added till the total weight achieved 10 kg, and uniform stirring was performed to get the citrus preservative of the embodiment; and the citrus preservative was used for soaking 'Shatang' mandarin fruit.

Embodiment 7

40 g of PHMG was mixed with 12 g of castor oil polyoxyethylene ether emulsifier EL-80, then 5 g of prochloraz and a small amount of water were added, uniform stirring was performed, water was finally added till the total weight achieved 10 kg, and uniform stirring was further performed to get the citrus preservative of the embodiment; and the citrus preservative was used for soaking 'Shatang' mandarin fruit.

Implementation Effect Test of the Citrus Preservative According to the Present Invention The preservatives were respectively prepared according to the above embodiments 1-7. 'Shatang' mandarin fruit were harvested in appropriate period. Any fruit with disease and mechanical damages were discarded. 'Shatang' mandarin fruit were respectively dipped in the above preservatives for 30 seconds and then slightly aired, and 'Shatang' mandarin fruit without soaking treatment were taken as the control. 'Shatang' mandarin fruit in all the experimental groups and the control group were packaged with polyethylene film bags with the thickness of 0.03 mm, placed in plastic baskets with 15 kg in each basket and stored at normal temperature (25° C.) for 45 days, the percentages of fruit decay were recorded, and the results are as shown in Table 1.

TABLE 1

Preservation Effect of Preservative disclosed by the Invention on 'Shatang' Mandarin Stored at Normal Temperature

| Group Name | Incidence Rate of Sour Rot (%) | Rot Rate (%) |
| --- | --- | --- |
| Embodiment 1 | 7.6 | 20 |
| Embodiment 2 | 0.7 | 3.7 |
| Embodiment 3 | 0 | 4.4 |
| Embodiment 4 | 4.5 | 9.1 |
| Embodiment 5 | 3.3 | 8.4 |
| Embodiment 6 | 8.3 | 10.6 |
| Embodiment 7 | 0.5 | 6.5 |
| Control Group | 60.1 | 85.8 |

What is claimed is:

1. A method for controlling citrus sour rot, comprising: applying a citrus preservative characterized in that calculated based on 100% total mass fraction, the citrus preservative comprises 0.05%-0.5% of polyhexamethylene guanidine hydrochloride, 0.05%-0.2% of imidazole fungicide, 0.02%-0.15% of quaternary ammonium salt emulsifier and the balance water.

2. A citrus preservative for inhibiting citrus sour rot, characterized in that calculated based on 100% total mass fraction, the citrus preservative comprises 0.05%-0.5% of polyhexamethylene guanidine hydrochloride, 0.05%-0.2% of imidazole fungicide, 0.02%-0.15% of quaternary ammonium salt emulsifier and the balance water.

3. The citrus preservative according to claim 2, characterized in that the mass fraction of polyhexamethylene guanidine hydrochloride is 0.1%-0.5%.

4. The citrus preservative according to claim 3, characterized in that the mass fraction of polyhexamethylene guanidine hydrochloride is 0.25%-0.5%.

5. The citrus preservative according to claim 2 characterized in that the imidazole fungicide is imazalil.

6. The citrus preservative according to claim 3, characterized in that the imidazole fungicide is imazalil.

7. The citrus preservative according to claim 4, characterized in that the imidazole fungicide is imazalil.

* * * * *